US007116340B2

(12) United States Patent
Van Liere

(10) Patent No.: US 7,116,340 B2
(45) Date of Patent: Oct. 3, 2006

(54) METHOD AND APPARATUS FOR SHORTHAND PROCESSING OF MEDICAL IMAGES, WHEREIN MOUSE POSITIONINGS AND/OR ACTUATIONS WILL IMMEDIATELY CONTROL INHERENT IMAGE PROCESSING FUNCTIONS, AND A PERTINENT COMPUTER PROGRAM

(75) Inventor: Filips Van Liere, Eindhoven (NL)

(73) Assignee: Koninklijke Philips Electronics, N.V, Eindhoven (NL)

( * ) Notice: Subject to any disclaimer, the term of this patent is extended or adjusted under 35 U.S.C. 154(b) by 320 days.

(21) Appl. No.: 09/864,128

(22) Filed: May 24, 2001

(65) Prior Publication Data

US 2002/0024530 A1 Feb. 28, 2002

(30) Foreign Application Priority Data

May 24, 2000 (EP) ................................. 00201841

(51) Int. Cl.
G09G 5/00 (2006.01)
G06F 17/00 (2006.01)
(52) U.S. Cl. ....................................... 345/619; 345/861
(58) Field of Classification Search ................ 345/619, 345/711, 708, 779, 781, 788, 847, 840, 634, 345/635; 715/711, 708, 779, 781, 788, 847, 715/840, 634, 635, 860, 861, 859
See application file for complete search history.

(56) References Cited

U.S. PATENT DOCUMENTS

| 4,586,035 | A | * | 4/1986 | Baker et al. ................. 345/157 |
|---|---|---|---|---|
| 5,001,697 | A | * | 3/1991 | Torres ........................ 715/542 |
| 5,425,137 | A | * | 6/1995 | Mohan et al. ............... 345/619 |
| 5,452,416 | A | * | 9/1995 | Hilton et al. ............... 715/783 |
| 5,553,225 | A | * | 9/1996 | Perry ......................... 345/786 |
| 5,608,774 | A | * | 3/1997 | Polichar et al. ............ 378/98.8 |
| 5,655,093 | A | * | 8/1997 | Frid-Nielsen ............... 715/856 |
| 5,745,109 | A | * | 4/1998 | Nakano et al. ............. 345/838 |
| 5,803,914 | A | * | 9/1998 | Ryals et al. ................ 600/407 |
| 5,898,432 | A | * | 4/1999 | Pinard ........................ 715/861 |
| 5,963,203 | A | * | 10/1999 | Goldberg et al. ........... 345/723 |
| 5,995,102 | A | * | 11/1999 | Rosen et al. ................ 715/856 |
| 6,018,332 | A | * | 1/2000 | Nason et al. ............... 345/661 |
| 6,067,085 | A | * | 5/2000 | Modh et al. ................ 715/711 |
| 6,084,598 | A | * | 7/2000 | Chekerylla .................. 345/441 |
| 6,128,010 | A | * | 10/2000 | Baxter et al. ............... 345/846 |
| 6,229,541 | B1 | * | 5/2001 | Kamen et al. .............. 715/719 |
| 6,232,972 | B1 | * | 5/2001 | Arcuri et al. ............... 345/815 |
| 6,236,389 | B1 | * | 5/2001 | Imaizumi et al. ........... 715/788 |
| 6,301,512 | B1 | * | 10/2001 | Motzer ....................... 700/90 |
| 6,337,702 | B1 | * | 1/2002 | Bates et al. ................. 715/857 |
| 6,411,274 | B1 | * | 6/2002 | Watanabe et al. ........... 345/684 |

(Continued)

FOREIGN PATENT DOCUMENTS

JP 63-298431 * 12/1988

(Continued)

OTHER PUBLICATIONS

T. Gunther et al, "Virim: A Massively Parallel Processor for Real-Time Volume Visualization in Medicine", Computers and Graphics, Pergamon Press Ltd, Oxford, GB, vol. 19, No., Sep. 1, 1995, pp. 705-510, XP004000244.

(Continued)

Primary Examiner—Ryan Yang

(57) ABSTRACT

A spatially displayed medical image undergoes processing through cursored user interaction on such image. In particular, mouse positionings and/or actuations will control inherent processing functionalities. These will actuate immediately through associated specific sensitive areas at predetermined relative positions with respect to an associated medical object display field.

21 Claims, 4 Drawing Sheets

U.S. PATENT DOCUMENTS

| | | | |
|---|---|---|---|
| 6,433,796 B1 * | 8/2002 | Taguchi | 345/753 |
| 6,473,094 B1 * | 10/2002 | Sheasby et al. | 345/629 |
| 6,535,233 B1 * | 3/2003 | Smith | 345/856 |
| 2001/0012017 A1 * | 8/2001 | Watanabe et al. | 345/619 |

FOREIGN PATENT DOCUMENTS

| WO | WO9511480 | 1/1994 |
|---|---|---|

OTHER PUBLICATIONS

J.A.Bixby, "A High-Speed Television System For Motion Analysis", SMPTE Journal, Jul. 1983, USA, vol. 92, No. 7, pp. 729-734, XP000997042.

Naonymous: "User Interface for Adjusting Video Source Area", IBM Technical Disclosure Bulletin, vol. 36, No. 9A, Sep. 1, 1993, pp. 449-451, XP000396125.

* cited by examiner

Grey-level windowing modes

Initial shutter sensitive area

Defined shutter sensitive area

METHOD AND APPARATUS FOR SHORTHAND PROCESSING OF MEDICAL IMAGES, WHEREIN MOUSE POSITIONINGS AND/OR ACTUATIONS WILL IMMEDIATELY CONTROL INHERENT IMAGE PROCESSING FUNCTIONS, AND A PERTINENT COMPUTER PROGRAM

BACKGROUND OF THE INVENTION

The invention relates to a method as recited in the preamble of claim 1. A frequent problem is the excessive mouse travel needed to activate functions. For example, an image zooming operation activated through a button on a toolbar could run as follows:
1. Move cursor to button on toolbar
2. Click on button to activate zoom function
3. Move cursor over image
4. Perform zoom interaction with respect to image.

Steps 1 to 3 are required because the toolbar button must be pressed prior to zooming. For a single dedicated operation this is tolerable, but when performing multiple operations on images the continual cursor movements to and from menu-bars, toolbars and or control panels become a nuisance.

On-screen toolbars and control panels cause distraction. The distraction increases with the amount of screen area reserved to user interface constructs. Workstation screen area is scarce and should only be used to display essential information. For routine and diagnostic viewing this is the display of medical images. The model hereinafter requires no user interface constructs other than a region on the screen to display an image and associated graphics overlays. Since no screen area is used by extraneous user-interface constructs, diagnostic-viewing applications can emulate a lightbox by using screen area predominantly for image display.

SUMMARY TO THE INVENTION

In consequence, amongst other things, it is an object of the present invention to provide access to various common image display manipulations without associating thereto user interface elements that would restrict screen area usable for displaying the image proper.

Now therefore, according to one of its aspects the invention is characterized according to the characterizing part of claim 1.

The invention also relates to an apparatus arranged for practising a method according to claim 1, and to a machine readable computer program for implementing a method as claimed in claim 1. Feasible transfer media would be Internet and various types of data carriers, such as floppy disks. Further advantageous aspects of the invention are recited in dependent Claims.

BRIEF DESCRIPTION OF THE DRAWING

These and further aspects and advantages of the invention will be discussed in more detail hereinafter with reference to the disclosure of preferred embodiments, and in particular with reference to the appended Figures that show.

DETAILED DESCRIPTION OF PREFERRED EMBODIMENTS

Figure 1:
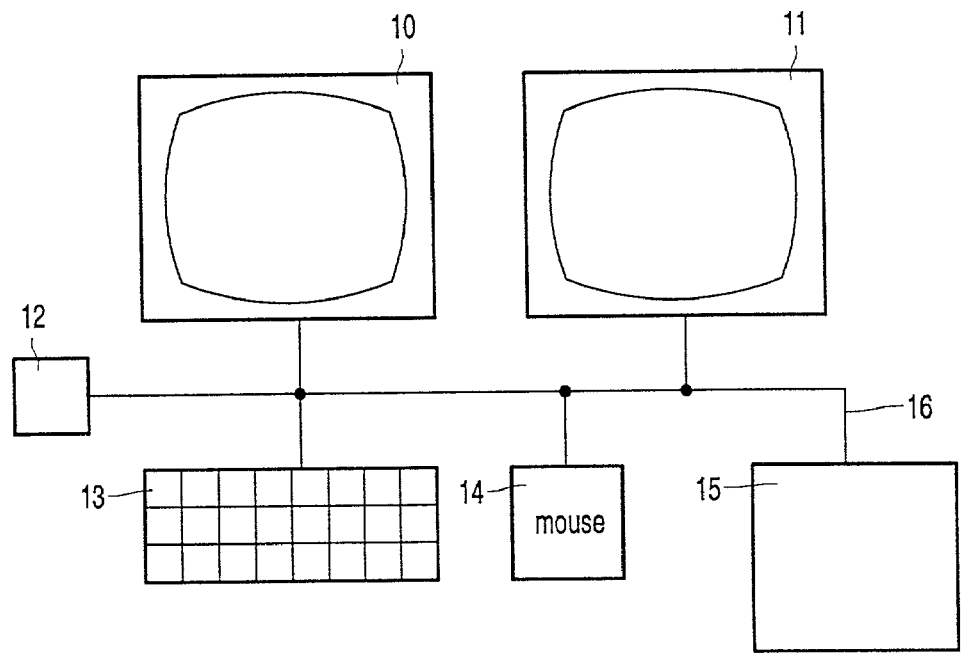
FIG. 1, a medical imaging arrangement.

FIG. 1 shows a medical imaging arrangement as pertaining to one or more conventional imaging technologies, such as CT, MRI, or other. The arrangement has two image monitors 10, 11, a keyboard 13, mouse 14, and a processor provided with appropriate storage 15. All these subsystems are interconnected through a suitable interconnection facility 16 that can be bus-based. I/O facility 12 interconnects to an outer world for receiving image data derived from the detection subsystem not shown for brevity, and for outputting of processed image data for long-term storage, hard-copying, and other. A user person may manipulate the image in various manners described hereinafter through mouse and/or keyboard actuations. Various other system configurations would be obvious to a person skilled in the art of image manipulating systems.

The following presents an interaction model for medical image viewing applications. It supports various image display functions. Most actions are single mouse-button. A few features use modifier keys. Full manipulation is directly on images and associated overlay graphics. A few control panels to set preferences or default behavior may enhance the user interface. The proposal features the following operations representing most of the operations performed on images during routine image viewing.

| Operation | Description |
| --- | --- |
| Window | Image pixel value to grey level display mapping |
| Zoom & pan | Image magnification and translation |
| Orientation | Flipping and rotating images |
| Shutter | Masking irrelevant image areas |
| Movie & scroll | Navigation through a sequence of images |

Simple operation is essential for applications used only occasionally, to avoid users getting confused. Providing a system controlled only by mouse is motivated in that virtually all systems on which viewing applications run have a mouse which is an extremely cost effective device.

Sensitive areas are used to interpret the interaction events. A sensitive area determines the meaning of a specific event such as a mouse click. Here, a user points at a specific sensitive area to perform a specific function. The advantage of sensitive areas for specific functions is that simply moving the cursor over the sensitive areas gives access to operations, keeping substantially all of the underlying image in view. All available operations are accessed via sensitive areas. The screen area on which images are displayed provides ample room for sensitive areas allocated to various routine-viewing operations.

Sensitive areas are supported through various visual cues in the form of graphics overlays and cursor shapes. Graphics overlays indicate where the sensitive areas are and the cursor shape will reflect the nature of the sensitive area under the cursor. The sensitive areas are chosen to coincide with graphics overlays used for the display image related information. For example, the sensitive area to flip an image coincides with the graphics used to indicate the orientation of the image. This saves screen area and makes the interaction intuitive.

The invention displays images in rectangular regions overlaid with various graphics objects. Such graphics objects are used for various purposes, such as:

| Overlay | Usage |
|---|---|
| Text | Image related attributes: patient name, exam date, procedure code |
| Calliper | Distance measure indicator |
| Orientation codes | Orientation of image relative to patient |
| Image number | Defines position in image sequence |
| Window values | Indicates displayed pixel value range |

The graphics objects are displayed near the edges of the display to avoid occluding the central area of the image where essential image information is usually concentrated. Many graphics objects directly correspond to display functions. For example, the zoom or magnification function alters the calliper display in such a way as to reflect the magnification of the image. This leads to allocating sensitive areas corresponding to graphics overlays.

| Overlay | Function |
|---|---|
| Calliper | Zoom |
| Orientation codes | Mirror and rotate |
| Image number | Scroll and movie |
| Window values | Grey value windowing |

Not all image display functions can be allocated in this manner. Edges of the region are allocated to shutters to allow shutters to be pulled out from the edge. The remaining display region is allocated to panning.

The interactions defined for an individual sensitive area depend on the function thereof. Display functions and graphics creation are treated separately hereinafter. Each sensitive area has an associated cursor shape that identifies the function of the sensitive area. At each sensitive area, the cursor assumes the associated shape as a visual cue to the user as to which function is associated.

Mouse interactions generally take one of two styles:
Click-Move-Click-The interaction is performed while no mouse button is pressed.
Press-Drag-Release -The interaction is performed while a mouse button is pressed.
The form chosen is a matter of taste. The click-move-click style has the advantage that the actual mouse motion is performed without a mouse button pressed enabling a finer control.
The press-drag-release style has the advantage that fewer mouse clicks are required.

Click-Move-Click
1. Move cursor to interaction position. Appropriate cursor displayed
2. Click mouse button. Optionally with one or more modifier keys.
3. Move cursor over screen. Interaction takes place.
4. Click mouse button.

Press-Drag-Release
1. Move cursor to interaction position. Appropriate cursor displayed.
2. Press button. Optional with one or more modifier keys.
3. Drag over screen. International takes place.
4. Release mouse button.

Actual interaction depends on the position where the mouse interaction is initiated and on the actuation of mouse buttons and modifier keys. Hereinafter, we assume the click-move-click style. All interactions can be readily converted to the press-drag-release style.

A few common image display functions performed during diagnostic image viewing are as follows. Grey-level windowing defines the mapping of a pixel value range to grey-level display values, by selecting either a specific pixel value range to be displayed for modalities with calibrated pixel values such as CT, or by optimizing contrast and brightness for a specific image feature. Mirror & rotate will flip or rotate images for orienting the image to a standard or preferred patient-related orientation, such as to compensate for incorrect insertion of a film cassette in a reader. Zoom & pan define the position and extent of a rectangular portion of the image to be displayed. Shutters will mask irrelevant or distracting image information at the image edge. Depending on image acquisition, it may contain artefacts or be saturated near the edge. Scroll & movie provide navigation through a sequence of images, through moving the cursor over the corresponding sensitive area and performing the relevant interaction. Each function will be detailed hereinafter.

Grey-level Windowing

There are three grey-level windowing modes:

| Mode | Usage | Modalities |
|---|---|---|
| Contrast/brightness | General purpose | All X-ray |
| Window width/level | Calibrated pixel-values & Large dynamic range | CT |
| Black/White level | Suppress background | MR, US |

Each mode defines the pixel-value to display grey-level mapping through two parameters, that are defined as follows:

| Parameter | Description |
|---|---|
| Contrast | Slope of grey-level mapping as percentage |
| Brightness | Mapping to centre distance as percentage |
| Window-width | Extent of mapped pixel-value range |
| Window-level | Pixel-value of centre of mapped pixel-value range |
| Black-level | Pixel-value of lower bound of mapped pixel-value range |
| White-level | Pixel-value of upper bound of mapped pixel-value range |

The contrast parameter defines the slope of the mapping in a range from 0° to 90°.

| Contrast | Slope | |
|---|---|---|
| 0 | 0° | Horizontal |
| 50 | 45° | Default |
| 100 | 90° | Vertical |

The brightness parameter defines the radius of a circle to which the linear grey-level mapping is tangent.

| Brightness | Mapping |
|---|---|
| 0 < B < 50 | Tangent in lower right |
| 50 | Passes through center |
| 50 < B < 100 | Tangent in upper left |

Grey-level mapping parameters are presented as two formatted values.

| Presentation | | Mapping |
|---|---|---|
| C55 | B47 | Contrast/brightness |
| W98 | L67 | Window-width/window-level |
| W330H | L120H | Calibrated window-width/window-level (CT) |
| B18 | W116 | Black-level/white-level |

Both grey-level mapping parameters have a sensitive area.

Contrast
1. Move cursor over contrast-sensitive area. Contrast cursor is displayed.
2. Press mouse button.
3. Drag cursor up or right to increase contrast, or drag cursor down or left to decrease contrast. Image contrast is adjusted. Cursor remains over sensitive area.
4. Release mouse button.

Alternatively:
1. Move cursor over contrast-sensitive area. Contrast cursor displayed.
2. Click to increase contrast. Shift-click to decrease contrast. Contrast modified by 10%.

Brightness
1. Move cursor over brightness sensitive area. Brightness cursor displayed.
2. Press mouse button.
3. Drag cursor up or right to increase brightness. Drag cursor down or left to decrease brightness. Image brightness adjusted. Cursor remains over sensitive area.
4. Release mouse button.

Alternatively:
1. Move cursor over brightness sensitive area. Brightness cursor displayed.
2. Click increases brightness. Shift-click decreases brightness. Brightness modified by 10%.

Contrast and Brightness
1. Move cursor over contrast or brightness sensitive area. Displays ContrastBrightness cursor.
2. Press mouse button with shift modifier.
3. Drag cursor right to increase, left to decrease contrast; up to increase, down to decrease brightness. Image contrast and brightness adjusted. Cursor remains over sensitive area.
4. Release mouse button.

Window-width
1. Move cursor over window-width sensitive area. Contrast cursor displayed.
2. Press mouse button.
3. Drag cursor up or right to increase window-width. Drag cursor down or left to decrease window-width. Image contrast adjusted. Cursor remains over sensitive area.
4. Release mouse button.

Alternatively:
1. Move cursor over window-width sensitive area. Contrast cursor displayed.
2. Click increases window-width by 10%; shift-click decreases window-width by 10%.

Window-level
1. Move cursor over window-level sensitive area. Brightness cursor displayed.
2. Press mouse button.
3. Drag cursor up or right to increase window-level. Drag cursor down or left to decrease window-level. Image brightness adjusted. Cursor remains over sensitive area.
4. Release mouse button.

Alternatively:
1. Move cursor over window-level sensitive area. Brightness cursor displayed.
2. Click to increase window-level. Shift-click to decrease window-level. Window-level modified with 25% of window-width.

Window-width and Window-level
1. Move cursor over width or level sensitive area. Contrast-Brightness cursor displayed.
2. Press mouse button with shift modifier.
3. Drag cursor right to increase width, left to decrease width, up to increase level, down to decrease level. Image contrast and brightness adjusted. Cursor stays over sensitive area.
4. Release mouse button.

Black-level
1. Move cursor over black-level sensitive area. Brightness cursor displayed.
2. Press mouse button.
3. Drag cursor up or right to increase black-level. Drag cursor down or left to decrease black-level. Image black-level adjusted. Cursor remains over sensitive area.
4. Release mouse button.

Alternatively:
1. Move cursor over black-level sensitive area. Brightness cursor displayed.
2. Click to increase black-level. Shift-click to decrease black-level. Level modified by 10%.

White-level
1. Move cursor over white-level sensitive area. Contrast cursor displayed.
2. Press mouse button.
3. Drag cursor up or right to increase white-level. Drag cursor down or left to decrease white-level. Image white-level adjusted. Cursor remains over sensitive area.
4. Release mouse button.

Alternatively:
1. Move cursor over white-level sensitive area. Contrast cursor displayed.
2. Click to increase white-level. Shift-click to decrease white-level. Level modified by 10%.

Black-level and White-level
1. Move cursor over black-or white-level-sensitive area. ContrastBrightness cursor displayed.
2. Press mouse button with shift modifier.
3. Drag cursor right to increase white-level, left to decrease white-level. Drag cursor up to increase black-level, down to decrease black-level. Image contrast and brightness adjusted. Cursor remains over sensitive area.
4. Release mouse button.

The mirror and rotate display functions are combined as they both define the display orientation of the image. The function uses two sensitive areas. The patient orientation code is displayed in the sensitive area for the user of the actual image orientation and locates the position of the corresponding sensitive areas. English language orientation codes are:

| Code | Patient direction |
|------|-------------------|
| H | Head |
| F | Feet |
| A | Anterior |
| P | Posterior |
| L | Left |
| R | Right |
| ? | Undefined |

Combinations of these codes may define oblique orientations. If an image carries insufficient information to determine the actual orientation, the "undefined" code is displayed. There are four mirror & rotate operations:

| Operation | Description |
|-----------|-------------|
| Mirror horizontal | Flips image right to left |
| Mirror vertical | Flips image top to bottom |
| Rotate clockwise | Rotates image 90° clockwise |
| Rotate counter-clockwise | Rotates image 90° counter-clockwise |

Interacting with the appropriate sensitive area performs these operations.

Mirror Horizontal
1. Move cursor over horizontal sensitive area. MirrorRotate cursor displayed.
2. Click to flip image right to left.

Mirror Vertical
1. Move cursor over vertical sensitive area. MirrorRotate cursor displayed
2. Click to flip image top to bottom.

Rotate Clockwise
1. Move cursor over vertical sensitive area. MirrorRotate cursor displayed
2. Press mouse button.
3. Drag cursor over horizontal sensitive area.
4. Release mouse button.

Alternatively:
1. Move cursor over vertical sensitive area. MirrorRotate cursor displayed
2. Click with shift modifier to rotate image 90° clockwise.

Rotate Counter-clockwise
1. Move cursor over horizontal sensitive area. MirrorRotate cursor displayed
2. Press mouse button.
3. Drag cursor over vertical sensitive area.
4. Release mouse button.

Alternatively:
1. Move cursor over horizontal sensitive area. MirrorRotate cursor displayed.
2. Click with shift modifier to rotate image 90° counter-clockwise.

Zoom & Pan
The zoom and pan functions together define a region of the image to be displayed. Zoom defines the extent of the region and pan the position of the region. The zoomed region has the same aspect ratio as the image display region; it may extend beyond the edges of the image. There are four zoom modes:

| Mode | Description |
|------|-------------|
| Fill region | Minimum zoom required to fill entire image display region |
| Entire image | Maximum zoom that displays entire image |
| True size | Unit distance in image mapped to unit distance on display |
| True pixel | Pixel in image mapped o pixel on display |

The mode can be set via a pop-up menu. The default mode is entire image. The zoom mode defines a nominal magnification applied during image display. The zoom sensitive area is integrated-with the display of the calliper. Manipulating the calliper zooms the image. Panning is performed directly on the image.

The calliper display reflects the actual magnification to transform a unit distance in the image to a unit distance on the display. The actual distance unit and the number of image pixels displayed per unit distance are displayed below the calliper. If an image carries insufficient information to perform this transformation, no distance unit is displayed. For example, the resolution of most RF images is not known unless explicitly calibrated.

Zoom
1. Move cursor over zoom sensitive area. Zoom cursor displayed.
2. Press mouse button.
3. Drag cursor to zoom image. Image is zoomed in or out as cursor is dragged.
4. Release mouse button. Calliper adjusted to reflect adjusted zoom.

To magnify the image (zoom in) the user conceptually increases the size of the calliper, increasing the image distance measure on the display. To zoom out, the user likewise decreases the size of the calliper and the image distance measure on the display. After zooming, the size of the calliper adjusts to about half the vertical size of the display region.

Pan
1. Move cursor over pan sensitive area. CrossHair cursor displayed.
2. Press mouse button.
3. Drag cursor to pan image. Image follows cursor during pan interaction.
4. Release mouse button.

The image will continue to pan even if the cursor is moved outside the pan sensitive area. There are five types of image shutters:

| Type | Description |
|------|-------------|
| Top | Masks top edge of image |
| Bottom | Masks bottom edge of image |
| Left | Masks left edge of image |

-continued

| Type | Description |
| --- | --- |
| Right | Masks right edge of image |
| Circular | Masks circular region of image |

Shutters may be combined to mask a selected region of the image. They are pulled out from the edges of the display region. If no shutter is defined, the sensitive areas are small or thin areas up against the corners or edges of the display region.

Top Shutter
1. Move cursor over top sensitive area. TopShutter cursor displayed.
2. Press mouse button.
3. Drag cursor downward to required position.
4. Release mouse button.

Bottom Shutter
1. Move cursor over bottom sensitive area. BottomShutter cursor displayed.
2. Press mouse button.
3. Drag cursor upward to required position.
4. Release mouse button.

Left Shutter
1. Move cursor over left sensitive area. LeftShutter cursor displayed.
2. Press mouse button.
3. Drag cursor to the right to required position.
4. Release mouse button.

Right Shutter
1. Move cursor over right sensitive area. RightShutter cursor displayed.
2. Press mouse button.
3. Drag cursor to the left to required position.
4. Release mouse button.

Circular Shutter
1. Move cursor over circular sensitive area. CircularShutter cursor displayed.
2. Press mouse button.
3. Drag cursor inward to required position.
4. Release mouse button.

Initial size and position of a circular shutter are chosen such that it intersects all four corners of the (rectangular) image display region.

Editing Shutters

Once a shutter is defined, its sensitive area is near the edge of the shutter. It follows the position of the shutter as the shutter is defined. Shutter edit interactions are similar to shutter creation interactions.
1. Move cursor over shutter sensitive area. Appropriate shutter cursor displayed.
2. Press mouse button.
3. Drag cursor to required shutter position.
4. Release mouse button.

Circular shutters have a diameter and a position that can be defined as follows:
1. Move cursor over circular sensitive area. CircularShutter cursor displayed.
2. Press mouse button with shift modifier.
3. Drag cursor inward to required position.
4. Release mouse button.

Shutters may not always be visible. For example, a circular shutter can be completely covered by top, bottom, left and right shutters. It may be necessary to first adjust one or more shutters to make a shutter visible in order to edit it.

Scroll & Movie

These operations assume that the images to be displayed form an ordered sequence. The image displayed is defined by the scroll position. The number of images in the sequence defines the sequence length and places an upper bound on the value of the scroll position. The scroll position ranges from 1 to the size of the sequence. If the sequence has only one image, scrolling is disabled. Scroll and movie actually provide three separate operations.

| Operation | Description |
| --- | --- |
| Paging | Incremental stepping through sequence |
| Scroll | Interactive positioning in sequence |
| Movie | Automated display of sequence |

Paging allows a user to step either to the next or to the previous image in the series.

Stepping to Next Image
1. Move cursor over scroll sensitive area. Scroll cursor displayed.
2. Click mouse button. Next image in sequence displayed. Image sequence position updated.

Stepping to Previous Image
1. Move cursor over scroll sensitive area. Scroll cursor displayed.
2. Click mouse button with shift modifier. Previous image in sequence displayed. Image sequence position updated.

Scroll
1. Move cursor over scroll sensitive area. Scroll cursor displayed.
2. Press mouse button.
3. Drag cursor up or right to increase scroll position, down or left to decrease scroll position.

Images corresponding to interactive scroll positions displayed. Image sequence position is updated as cursor is dragged. Cursor remains over scroll sensitive area.
4. Release mouse button.

Starting and stopping controls the movie.

Starting Movie
1. Move cursor over scroll sensitive area. Scroll cursor displayed.
2. Double click mouse button. Movie starts. Successive images in sequence displayed. Image sequence position updated as movie runs.

Stopping Movie
1. Move cursor over scroll sensitive area. Scroll cursor displayed.
2. Click mouse button. Movie stops.

The movie can be set in one of three modes, selected e.g. by a pop-up menu on the image

| Mode | Description |
| --- | --- |
| Forward | Cyclically displays images in sequence order |
| Reverse | Cyclically displays images in reverse sequence order |
| Bounce | Alternately displays images in forward and reverse sequence order |

Sensitive areas give a mode-less interaction. However, pointing accuracy is limited, because sensitive areas are kept relatively small to avoid cluttering the display region. This requires some attention and dexterity from the user person. Further, moving the cursor to a sensitive area requires mouse motion. This may cause too much moving if various interleaved interactions are performed. Both problems distract from the image viewing proper. For selected operations this may be overcome by allocating the left mouse button to a specific interaction, such as simply dragging over the image. The interaction may then be performed independent of the cursor location in the display. The basic interaction is:

1. Move cursor over display, not positioned over a sensitive area. Display CrossHair cursor.
2. Click to activate allocated interaction. Appropriate cursor displayed.
3. Move cursor over image to modify allocated parameter(s). Parameter value(s) updated as cursor is moved, and image display updated to reflect modified parameter value(s).
4. Click to terminate interaction. CrossHair cursor redisplayed.

The interactions suitable to allocated mouse interaction are grey-level windowing, scrolling, zooming and panning.

| Interaction | Direction | Description |
| --- | --- | --- |
| Grey-level | Left | Decrease Contrast, Window width or White level |
| | Right | Increase Contrast, Window width or White level |
| | Down | Decrease Brightness, Window level or Black level |
| | Up | Increase Brightness, Window level or Black level |
| Scroll | Left | Scroll to previous image |
| | Right | Scroll to next image |
| | Down | Scroll to previous image |
| | Up | Scroll to next image |
| 2D Scroll | Left | Scroll to previous image column |
| | Right | Scroll to next image column |
| | Down | Scroll to previous image row |
| | Up | Scroll to next image row |
| Zoom | Left | Decrease magnification |
| | Right | Increase magnification |
| | Down | Decrease magnification |
| | Up | Increase magnification |
| Pan | Left | Pan image left |
| | Right | Pan image right |
| | Down | Pan image down |
| | Up | Pan image up |

The amount by which an allocated parameter value is modified, is defined by the sensitivity of the interaction: the amount of value change per unit distance of cursor moving. The sensitivity should be independent of the size of the region or the resolution of the display so that value changes will feel the same under varying circumstances. Sensitivity may be defined as follows:

| Value | Sensitivity |
| --- | --- |
| Contrast | 5%/cm |
| Brightness | 5%/cm |
| Window width | 5%/cm |
| Window level | 10% of window width/cm |
| Black level | 5%/cm |
| White level | 5% of difference with black level/cm |
| Zoom | 10%/cm |
| Scroll | 1 image/cm |

Moving the cursor over the associated sensitive area and clicking performs the actual allocation. The sensitive area is highlighted to indicate the allocated parameter value.

For example, to allocate grey-level windowing:

1. Move cursor over Contrast or Brightness sensitive area displays appropriate cursor.
2. Click to allocate grey-level windowing. Highlight Contrast and Brightness sensitive areas.
3. Move cursor over image. Cross Hair cursor is displayed
4. Click to start grey-level windowing. ContrastBrightness cursor displayed.
5. Move cursor over image. Grey-level parameters modified. Image display updated to reflect modified grey-level mapping.
6. Click to terminate interaction. CrossHair cursor displayed.

Steps 4, 5 and 6 may be repeated to perform successive grey-level interactions.

Keyboard Operation

An IntelliMouse is a pointing device with three buttons and a wheel, the middle button activated by pressing on the wheel. The wheel allows to set a numeric parameters such as contrast and brightness values by turning (rolling) the wheel. Basic interaction is as follows:

1. Move cursor over parameter sensitive area. Appropriate cursor displayed.
2. Turn wheel outward to increase value. Turn wheel inward to decrease value. Parameter value updated as wheel is turned. Image display updated to reflect modified parameter value.

The wheel is turned in steps, each corresponding to an incremental modification of the value in question. The change for one step depends on the parameter values modified.

| Value | Step size |
| --- | --- |
| Contrast | 5% |
| Brightness | 5% |
| Window width | 5% |
| Window level | 10% of window width |
| Black level | 5% |
| White level | 5% of difference with black level |
| Zoom | 10% |
| Scroll | 1 |

Sensitivity may be set via a property panel. A further facility of the IntelliMouse allows grey-level windowing, zoom or scroll, and pan simultaneously directly on the image.

| Button | Direction | Description |
| --- | --- | --- |
| Left | Left | Decrease Contrast, Window width or White level |
| Left | Right | Increase Contrast, Window width or White level |
| Left | Down | Decrease Brightness, Window level or Black level |
| Left | Up | Increase Brightness, Window level or Black level |
| Wheel | Outward | Increase zoom or Next image |
| Wheel | Inward | Decrease zoom or Previous image |
| Middle | All | Pan image |

The allocation of zoom or scroll to the wheel depends on the serializing of the images; scroll applies if a series is displayed and zoom if a single image is displayed. This does not conflict with the capability mentioned earlier of setting parameter values via the wheel. This is still possible by moving the cursor over the appropriate sensitive area.

Figure 2:
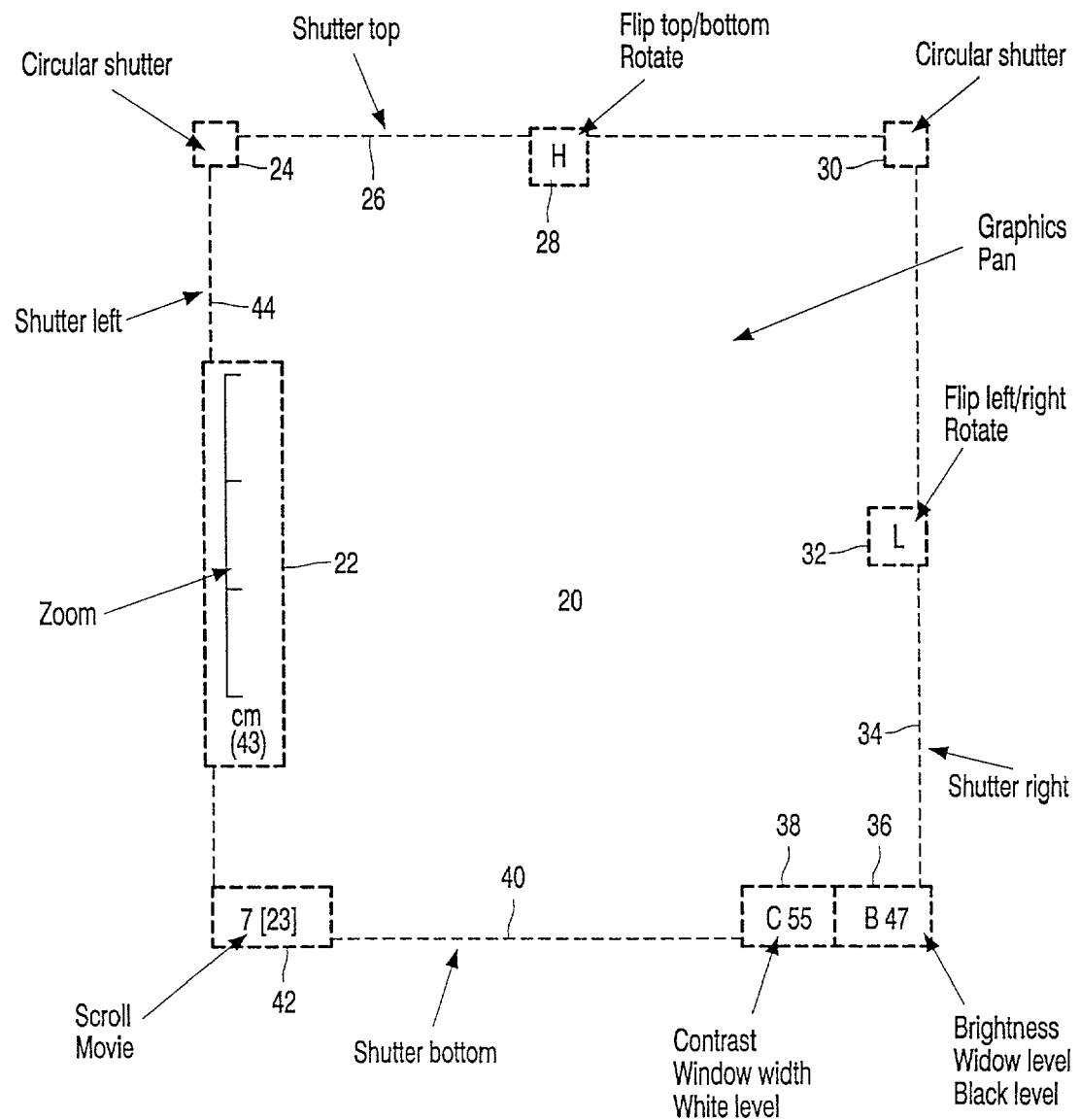
FIG. 2, an applicable image field with sensitive areas.

As regarding the Figures in particular, FIG. 2 illustrates an applicable image field with sensitive areas. The field 3 need not be to scale. All sensitive areas except one lie at the edges of the image field. The latter, 20, controls image panning but does effectively not obscure the user image. Furthermore, items 24 and 30 control a circular shutter, 28 (H) controls top/bottom flipping and rotating, 32 (L) controls left/right flipping through rotating, item 34 controls right shutter, 36 selectably controls brightness, window level or black level, 38 selectably controls contrast, window width or white level, 40 controls bottom shutter, 42 selectably controls scroll and movie, 22 controls zoom, and item 44 controls shutter left.

Figures 3A, 3B, 3C:
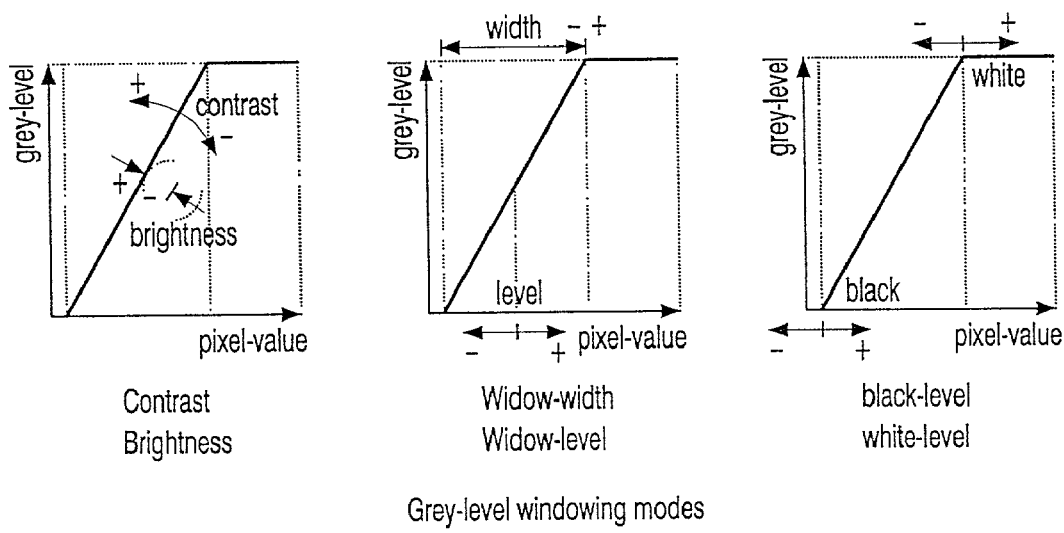
FIGS. 3*a*, 3*b*, 3*c* indicate three respective grey-level windowing modes.

FIGS. 3*a*, 3*b*, 3*c* indicate three respective grey-level windowing modes. Herein, FIG. 3*a* illustrates selecting contrast and/or brightness windows. The grey-level is a function of the pixel value. Selectably rotating towards a steeper edge produces much contrast for limited differences of pixel values, but operates only in a narrow interval of pixel values, and vice versa. Selectably moving the edge to the left increases the overall brightness of the picture, as many pixels with the pixel values in the left hand region get maximum brightness, and vice versa. Note that the two variable in FIG. 3*a* may be operated simultaneously.

FIG. 3*b* illustrates selecting of window width and window level. Selectably amending the width to a greater value generally produces more pixels with intermediate grey-level values, and vice versa. Selectably amending the window level to the left produces more pixels at less than the maximum grey level, and vice versa.

FIG. 3*c* illustrates the selecting of black and white levels. Of course, a white level, i.e. a pixel value that produces a white image pixel must always lie at a higher pixel value than a black level, i.e. a pixel value that produces a black image pixel. For the remainder, the interval between the two selectable pixel values can be chosen arbitrarily. In the above, next to the usage of straight lines, the slope may be produced in the manner of an "s" or similar curve. As to the latter, this may be produced by two selectable parameter values.

Figure 4:
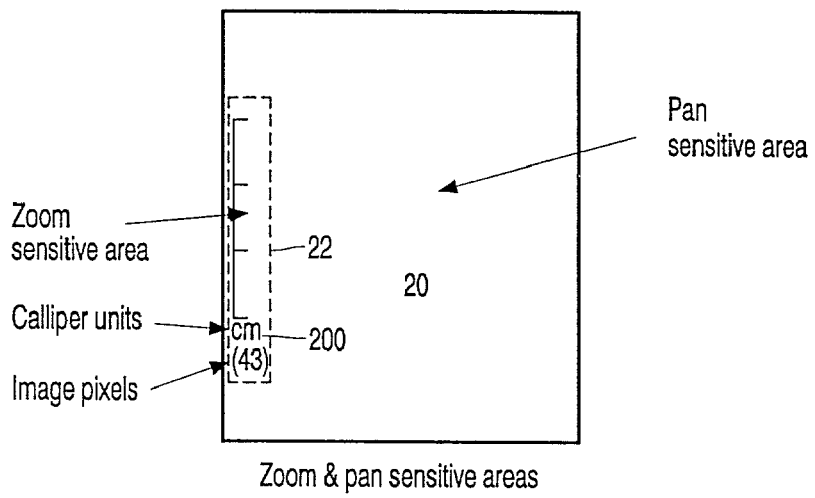
FIG. 4 illustrates zoom and pan sensitive areas.

FIG. 4 shows in particular zoom and pan sensitive areas. Items 20, 22 already show in FIG. 2. Item 200 indicates the calliper units (top indication of measuring units). The bracketed numeral indicates the number of pixels taking place in the operation.

Figure 5:
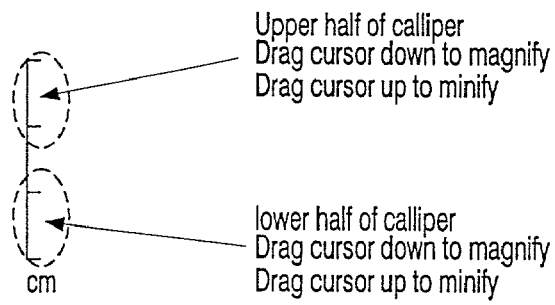
FIG. 5 illustrates manipulating the calliper during zoom.

FIG. 5 shows manipulating the calliper during zoom. The slightly greater complexity of the design was found advantageous. Clicking and dragging to the upper half of the calliper respectively magnify or minify the calliper size. For the lower half the changes are inverse.

Figure 6:
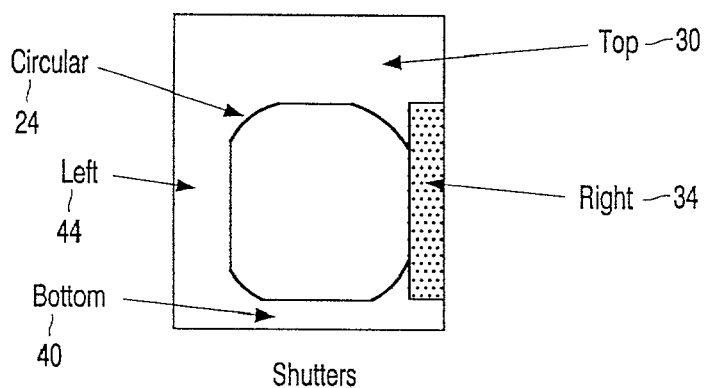
FIG. 6 illustrates various shutters in detail.
Figure 7:
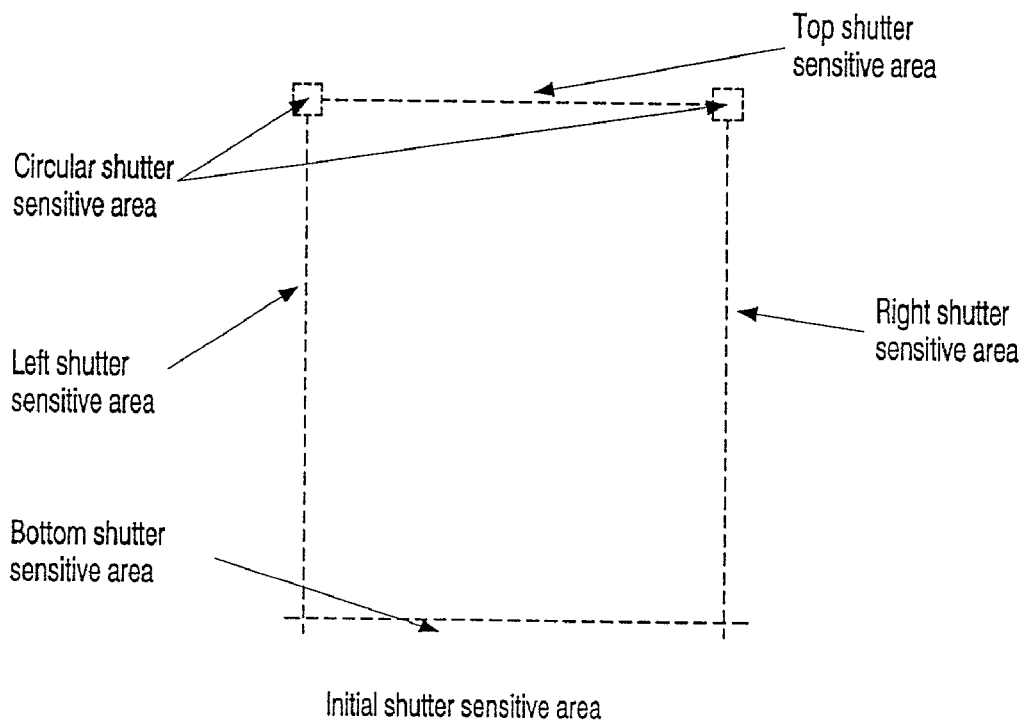
FIG. 7 illustrates various initial shutter sensitive areas.
Figure 8:
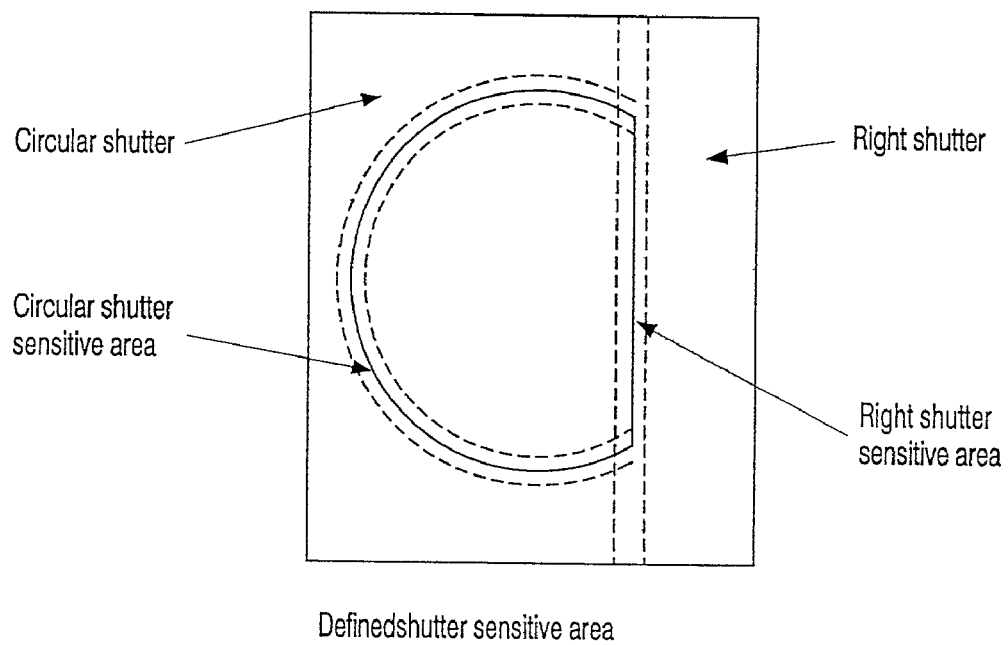
FIG. 8 illustrates defined shutter sensitive area.

FIG. 6 illustrates various shutters in detail. Herein, the showing more or less corresponds to that of FIG. 3, the right shutter been active. FIG. 7 illustrates various self-explanatory various initial shutter sensitive areas. FIG. 8 illustrates the sizes of various defined shutter sensitive areas, including sensitivity thereof.

Persons skilled in the art will recognize that the above disclosed method may be stored on a data carrier as a computer program that can effect or enhance an existing image processing machine to attain features of the present invention.

The invention claimed is:

1. A method for providing and processing a cursored user interaction, said method comprises the steps of:
   providing a menu-less graphical interface having a plurality of sensitive areas, each sensitive area is positioned at a predetermined, fixed relative position with respect to an associated medical image display field and with respect to at least one additional sensitive area, wherein each of the plurality of sensitive areas corresponds to at least one function and is associated with one of a plurality of different cursors providing a visual cue as to the at least one function corresponding to each of the plurality of sensitive areas;
   spatially displaying a medical image in said field; and,
   while said image continues to be displayed, controlling a mouse configured such that positionings of said mouse within each of said plurality of sensitive areas causes display of one of the plurality of different cursors and allows activation and control of a plurality of inherent processing functionalities for performing the at least one function respectively associated with each of said plurality of sensitive areas, said at least one function comprising image processing on said spatially displayed medical image, said controlling positioning said mouse within an area from among said areas to cause said display and allow said activation and control.

2. A method as claimed in claim 1, wherein performing said image processing comprises selecting grey range and/or color range windowing through geometrical mouse positioning.

3. A method as claimed in claim 1, wherein performing said image processing comprises selecting image mirror or rotation transformations.

4. A method as claimed in claim 1, wherein performing said image processing comprises selecting image zoom or pan transformations.

5. A method as claimed in claim 1, wherein performing said image processing comprises selecting shutter masking of the display field.

6. A method as claimed in claim 1, wherein performing said image processing comprises selectably navigating through a sequence of images that base on marginal stepping with respect to an imaged object.

7. An apparatus for providing and processing cursored user interactions, said apparatus comprising:
   a menu-less graphical interface having a plurality of sensitive areas, each sensitive area is positioned at a predetermined, fixed relative position with respect to an associated medical image display field and with respect to at least one additional sensitive area, wherein each of the plurality of sensitive areas corresponds to at least one function and is associated with one of a plurality of different cursors providing a visual cue as to the at least one function corresponding to each of the plurality of sensitive areas;

a mouse configured such that positionings of said mouse within each of said plurality of sensitive areas causes display of one of the plurality of different cursors and allows activation and control of a plurality of inherent processing functionalities for performing, while a medical image continues to be spatially displayed in said field, the at least one function respectively associated with each of said plurality of sensitive areas, said at least one function comprising image processing on the spatially displayed medical image, said controlling positioning said mouse within an area from among said areas to cause said display and allow said activation and control; and display means dimensioned for displaying said medical image and said menu-less graphical interface.

8. An apparatus as claimed in claim 7, and having selection means for performing said image processing by selecting grey range and/or color range windowing through geometrical mouse positioning.

9. An apparatus as claimed in claim 7, and having selection means for performing said image processing by selecting image mirror or rotation transformations.

10. An apparatus as claimed in claim 7, and having selection means for performing said image processing by selecting image zoom or pan transformations.

11. An apparatus as claimed in claim 7, and having selection means for performing said image processing by selecting edged shutter masking of the display field.

12. An apparatus as claimed in claim 8, and having navigation means for performing said image processing by selectably navigating through a sequence of images that base on marginal stepping with respect to an imaged object.

13. A machine-readable computer program, said program being arranged for providing and processing a cursored user interaction, said computer program comprising the steps of:

providing a menu-less graphical interface having a plurality of sensitive areas, each sensitive area is positioned at a predetermined, fixed relative position with respect to an associated medical image display field and with respect to at least one additional sensitive area, wherein each of the plurality of sensitive areas corresponds to at least one function and is associated with one of a plurality of different cursors providing a visual cue to the at least one function corresponding to each of the plurality of sensitive areas;

spatially displaying a medical image in said field; and, while said image continues to be displayed, controlling a mouse configured such that positionings of said mouse within each of said plurality of sensitive areas causes display of one of the plurality of different cursors and allows activation and control of a plurality of inherent processing functionalities for performing the at least one function respectively associated with each of said plurality of sensitive areas, said at least one function comprising manipulating the spatially displayed medical image, said controlling positioning said mouse within an area from among said areas to cause said display and allow said activation and control.

14. The method of claim 1, comprising the step of, responsive to said positioning, executing said performing of a function from among said at least one function to thereby perform said image processing.

15. The method of claim 1, such that continuous movement of said mouse, and consequently an on-screen cursor, in a direction, from a center of said field, toward an area from among said plurality of sensitive areas causes, upon entering said area, display of a respective one of said plurality of different cursors and allows said activation and control of a respective one of said plurality of inherent processing functionalities, said spatially displayed medical image being located in said field and, in relation to said area, in a direction opposite to said direction toward said area.

16. The method of claim 1, wherein said image processing comprises manipulating said medical image for diagnostic viewing.

17. The apparatus of claim 7, wherein said image processing comprises manipulating said medical image for diagnostic viewing.

18. A method for providing and processing a cursored user interaction with a spatially displayed medical image and performing image processing on said medical image, said method comprising:

providing a menu-less graphical interface having a plurality of sensitive areas respectively positioned at predetermined, fixed relative positions with respect to an associated medical image display field, at least two of the areas being positioned at predetermined, fixed relative positions with respect to each other, the plural sensitive areas corresponding to respective functions and being associated with respective ones of a plurality of different cursors that each provide a visual cue as to an associated function from among said respective functions; and controlling a mouse having an on-screen cursor and configured such that continuous movement of said cursor in a direction, from a center of said field, toward an area from among said plural sensitive areas causes, upon entering said area, display of a respective one of the plurality of different cursors and allows activation and control of a plurality of inherent processing functionalities for performing a corresponding function from among said respective functions, said performing of said corresponding function occurring on said spatially displayed medical image which is located in said field and, in relation to said area, in a direction opposite to said direction toward said area, said corresponding function comprising image processing on said spatially displayed medical image.

19. The method of claim 18, further comprising spatially displaying a medical image that constitutes said spatially displayed medical image, and subsequently executing said performing.

20. The method of claim 19, comprising executing, while said spatially displayed medical image continues to be displayed, said continuous movement of said cursor.

21. The method of claim 18, wherein said image processing comprises manipulating said medical image for diagnostic viewing.

* * * * *